(12) United States Patent
Romari

(10) Patent No.: US 12,203,121 B2
(45) Date of Patent: Jan. 21, 2025

(54) PROTISTS ENRICHED WITH LIPIDS RICH IN POLYUNSATURATED FATTY ACIDS

(71) Applicant: BIOREA, Lamballe-Armor (FR)

(72) Inventor: Khadidja Romari, Saint Ouen (FR)

(73) Assignee: BIOREA, Lamballe-Armor (FR)

( * ) Notice: Subject to any disclaimer, the term of this patent is extended or adjusted under 35 U.S.C. 154(b) by 47 days.

(21) Appl. No.: 17/817,113

(22) Filed: Aug. 3, 2022

(65) Prior Publication Data

US 2022/0372430 A1 Nov. 24, 2022

Related U.S. Application Data

(62) Division of application No. 16/061,502, filed as application No. PCT/FR2016/053359 on Dec. 13, 2016, now Pat. No. 11,427,799.

(30) Foreign Application Priority Data

Dec. 14, 2015 (FR) ...................................... 1562310

(51) Int. Cl.
| | |
|---|---|
| C12N 1/12 | (2006.01) |
| A23K 20/158 | (2016.01) |
| A23L 33/115 | (2016.01) |
| A61K 8/9706 | (2017.01) |
| C12P 7/6427 | (2022.01) |
| C12P 7/6434 | (2022.01) |

(52) U.S. Cl.
CPC .......... *C12P 7/6434* (2022.01); *A23K 20/158* (2016.05); *A23L 33/115* (2016.08); *A61K 8/9706* (2017.08); *C12N 1/12* (2013.01); *C12P 7/6427* (2013.01); *A23V 2002/00* (2013.01)

(58) Field of Classification Search
None
See application file for complete search history.

(56) References Cited

U.S. PATENT DOCUMENTS

| 9,017,985 B2 | 4/2015 | Kudla et al. |
| 2010/0291053 A1 | 11/2010 | Clayton et al. |
| 2011/0165658 A1 | 7/2011 | Kudla et al. |
| 2013/0217085 A1 | 8/2013 | Huang et al. |
| 2015/0037838 A1 | 2/2015 | Romari et al. |
| 2017/0016036 A1 | 1/2017 | Calleja et al. |

FOREIGN PATENT DOCUMENTS

| CN | 101168501 A | 4/2008 |
| CN | 102511818 A | 6/2012 |
| CN | 104185678 A | 12/2014 |
| RU | 2199582 C2 | 10/2000 |
| WO | 2006050975 A1 | 5/2006 |
| WO | 2013010090 A2 | 1/2013 |
| WO | 2015150716 A2 | 10/2015 |

OTHER PUBLICATIONS

Gennity J M et al., "A selenite-induced decrease in the lipid content of a red alga" Phytochemistry, pp. 2823-2283, vol. 24, No. 12 (Nov. 1985).
Andrew E Wheeler et al., Elsevier Biomedical Press the Effect of Selenate, Selenite, and Sulfate on the Growth of Six Unicellular Marine Algae, Mar. Biol. Ecol, pp. 181-194, (Jan. 1982).
Yu et al., "Chemicals to enhance microalgal growth and accumulation of high-value bioproducts", Frontiers in Microbiology FoodMicrobiology, pp. 1-10, {Feb. 2015).
Ren et al., "Enhanced docosahexaenoic acid production by reinforcing acetv-CoA and NADPH supply in *Schizochytrium* sp. HX-308", Bioprocess and Biosystems Engineering, one page—abstract.
ReportsnReports.com, "Omega-3 PUFA Markel by Type (DHA, EPA, ALA), Source[Marine (Fish, Algal, Krill, others), Plant (Flaxseed, Chia Seed, Others)], Application (Dietary supplement, Functional F&B, Pharma, Infant Formula, Others) & Geography— Global Trend & Forecast to 2019", pp. 1-3 (2019) (Abstract only).
McKenzie et al., "Selenium and the Regulation of Cell Signaling, Growth, and Survival: Molecular and Mechanistic Aspeci", Antioxidants & Redox Signaling, pp. 339-351, vol. 4, No. 2 (2002).
Liu et al., "Investigation of selenium pretreatment in the attenuation of lung injury in rats induced by fine particulate matters", Environ Sci Pollut Res., pp. 1-10 (Dec. 2016).
Li et al., "Bioeffects of selenite on the growth of Spirulina plalensis and its biotransformalion", Bioresource Technology, pp. 171-176, vol. 89 (Jan. 2003).
Guan et al., "Enhancement of Polyunsaturated Fatty Acid Production by Selenium Treatment in Polyunsaturated Fatty Acid-Producing Fungus", J Am Oil Chem Soc, pp. 1309-1317, vol. 87 (Jun. 2010).
Dasilva et al., "Effect of n-dodecane on Crypthecodinium cohnii fermentations and DHA production", J Ind Microbiol Biolechnol, pp. 408-416, vol. 33 (Feb. 2006).
Chin et al., "Schizochytrium limacinum SR-21 as a source of docosahexaenoic acid: optimal growth and use as a dietary supplement for laying hens", Australian Journal of Agricultural Research, pp. 13-20, vol. 57 (2006).
Certik et al., "Effect of Selenium on Lipid Alternations in Pigment-forming Yeasts", Food Sci. Biolechnol., pp. 45-51, vol. 22(S) (Feb. 2013).

(Continued)

Primary Examiner — Jennifer E Graser
(74) Attorney, Agent, or Firm — FISHERBROYLES, LLP; Roger L. Browdy

(57) ABSTRACT

The invention relates to a method for enriching protists with lipids rich in polyunsaturated fatty acids (PUFA) in particular of the omega 3 (ω3) class, said method comprising the culture of protists in a culture medium comprising a selenium-containing compound as well as the protists enriched with lipids rich in PUFA obtained by this method.
The invention also relates to a method for producing lipids rich in PUFA, comprising, after the enrichment method according to the invention, a method for treating the protists by extraction from the biomass of selenium-containing lipids rich in PUFA.
The invention finally relates to any food, cosmetic or pharmaceutical product comprising either selenium-containing lipids thus extracted, or selenium-containing biomass originating from the enrichment method.

19 Claims, 2 Drawing Sheets

(56) References Cited

OTHER PUBLICATIONS

Bumbak et al., "Best practices in heterotrophic high-cell-density microalgal processes: achievements, potential and possible limitations", Appl Microbiol Biotechnol, pp. 31-46, vol. 91 (May 2011).
Bligh et al., "A Rapid Method of Total Lipid Extraction and Purification", Canadian Journal of Biochemistry and Physiology, pp. 911-917, vol. 37, No. 8 (Aug. 1959).

PROTISTS ENRICHED WITH LIPIDS RICH IN POLYUNSATURATED FATTY ACIDS

The invention relates to a method for enriching protists, preferably microalgae, with lipids rich in polyunsaturated fatty acids, in particular of the omega 3 (ω3) class, said method comprising the culture of protists in a culture medium comprising at least one selenium-containing compound, and to the enriched protists thus obtained, as well as to a method for producing lipids rich in polyunsaturated fatty acids, in particular of the ω3 class, implementing the enrichment method according to the invention.

The present invention relates to the general field of the production of fatty acids by means of microorganisms, in particular protists, very particularly microalgae. The term "protists" denotes eukaryotes other than animals, fungi and plants. This group is highly heterogeneous and brings together organisms with a cell organization called simple, unicellular organisms (most common) or multicellular organisms without specialized tissues. Certain protists are autotrophic and others are heterotrophic (such as protozoa feeding on microalgae or microalgae of the genus *Schizochytrium* or of the genus *Crypthecodinium*).

Polyunsaturated fatty acids (PUFA) form part of the main constituents of the lipids in biological systems. A PUFA is formed of a hydrocarbon-containing chain containing at least 18 carbon atoms per molecule, terminated by a carboxyl group, and contains at least two carbon-carbon double bonds.

PUFAs are classified according to their carbon number, their number of unsaturations (or carbon-carbon double bonds) and the position of their first unsaturation starting from the group opposite the carboxyl group. Thus, a polyunsaturated fatty acid C X:Y ωZ is a fatty acid containing X carbon atoms, Y unsaturations and the first unsaturation of which is in $Z^{th}$ position i.e. position No. Z, where X, Y and Z are each an integer, X being greater than or equal to 18.

The two most important classes of PUFA are the omega 3 (ω3) and omega 6 (ω6) classes.

Among the PUFAs of the ω3 class are α-linolenic acid (C 18:3 ω3), eicosapentaenoic acid (or EPA) (C 20:5 ω3) and docosahexanoic acid (or DHA) (C 22:6 ω3).

DHA has six unsaturations in total at positions 3, 6, 9, 12, 15 and 18.

In general, PUFAs are essential for the growth and survival of all organisms in maintaining the integrity of membranes, in maintaining the permeability of membranes and in the storage of cellular carbon. Mammals that do not have the enzymes necessary for their synthesis must therefore find them in their food.

In humans, PUFAs play an essential role in the development and optimal functioning of the brain, the heart and many other organs and tissues. In particular, PUFAs of the ω3 class are presented as the most beneficial compounds for human health in the long term, as they reduce the risk of cardiovascular illnesses and immunological and inflammatory disorders. They would also act on the brain system, the hormonal system and the inflammatory system. DHA, in particular, allows good fetal and infantile development at the visual and neurological level, which over the last few years has given it increasing importance in different formulations of food products, in particular foods for infants.

Thus, the market for PUFAs of the ω3 class exceeded 2 billion dollars in 2014. According to the market study «*Omega-3 PUFA Market by Type (DHA, EPA, ALA), Source [Marine (Fish, Algal, Krill, Others), Plant (Flaxseed, Chia Seed, Others)], Application (Dietary supplement, Functional F&B, Pharma, Infant Formula, Others) & Geography—Global Trend & Forecast to* 2019», this market would exceed 4 billion dollars in 2019. Certain foods are naturally rich in them, such as oily fish (herrings, sardines, mackerels etc.) and certain vegetable oils (rape seed, nut, soybean etc.). However, although fish oils currently represent the main industrial source of PUFAs, they can no longer continue to cope with the increase in demand, in particular for DHA. In fact, the sustained demand for high-quality fish oils should be seen in the context of over-fishing, leading to the introduction of increasingly strict regulations on fishing, and a reduction in the overall production of fish oil. The production of fish oils also poses problems of refining, in particular due to the unpleasant taste and smell of these fish oils, their poor oxidative stability and their content of cholesterol and toxic products. Therefore, their use has been limited, in particular in the food supplement market.

Consequently, an alternative source is beginning to be used for this growing market for the production of PUFA: microorganisms, in particular microalgae. In fact, the latter, by means of their extraordinary diversity and their metabolic plasticity, represent an important source of PUFA for numerous industries, in particular the food and pharmaceutical industries. Among these microorganisms, in particular are found microalgae of the protists kingdom such as the family Thraustochytrids, comprising the genus *Schizochytrium* and the family Dinoflagellata (Dinoflagellates) comprising the genus *Crypthecodinium*. The fatty acids composition of microalgae is often simpler than that of fish oils, reducing the number of steps necessary in order to concentrate the fatty acids sought. The microalgae *Schizochytrium* and *Crypthecodinium* are capable of producing lipids in a quantity up to 40-50% of their dry biomass and up to 30-40% of PUFA from the total lipids. These PUFA are mainly stored in the form of triglycerides. Moreover, these marine microalgae do not have an unpleasant smell as they do not comprise cholesterol, and thus do not have the drawbacks presented by fish oils. They are also well perceived by consumers as a natural product of vegetable origin. It is also possible to produce microalgae on a large scale in bioreactors by monitoring all of the culture parameters. As a result, microalgae are now at the forefront of sources of PUFA, as an alternative to fish oils.

DHA is in particular used in formulations for infants and premature babies, and in food supplements. It can originate from aquaculture using the heterotrophic marine microalgae *Crypthecodinium* and *Schizochytrium*.

The culture conditions of the microalgae have a significant influence on PUFA yields. However, although the quantities of biomass obtained vary greatly, it is noted that the proportions of EPA and DHA, with respect to this biomass, remain constant overall. One of the routes explored in order to improve the growth and production of high-added value molecules such as lipids and carotenoids in microalgae is supplementing the culture medium of these microalgae with chemical compound(s).

Thus, the patent application US 2013/0217085 teaches that the addition of exogenous glycine betaine or trehalose to the culture medium can significantly increase the fermentation yield of polyunsaturated fatty acids from *Schizochytrium*, in particular *Schizochytrium limacinum*; the addition of n-dodecane (oxygen carrier) to the culture medium of *Crypthecodinium cohnii* made it possible to increase the production of DHA to reach 51% of total lipids, as reported in the publication Da Silva et al., «*Effect of n-dodecane on Crypthecodinium cohnii fermentations and DHA production*», J. Ind. Microbiol. Biotechnol. 33 pp 408-416, 2006.

However, apart from the negative image given to consumers by the use of non bio-sourced (i.e. not of vegetable origin) chemical compounds, the addition of these compounds, as well as being costly, poses problems of purification of the microalgae as they are found in the final biomass.

On the other hand, patent application WO 2015/15071.6 describes a method for the culture of microalgae of the genus *Aurantiochytrium*, in particular a protist of the genus *Aurantiochytrium mangrovei*, in a culture medium substantially free from chloride and substantially free from sodium, for the production of DHA. The strains concerned are strains of Thraustochytrids of the genus *Aurantiochytrium mangrovei* and *Aurantiochytrium limacinum*. Selenium is mentioned, among many other elements, as a carrier of sodium optionally able to be present in very low quantities in the culture medium (not more than 1 mg/L of sodium selenite, i.e. not more than 0.46 mg/L of selenium). Moreover, it is indicated that the strains *Schizochytrium* sp. are not expressly part of the invention.

Finally, the document WO 2013/010090 describes compositions with a high lipid content, as well as methods for their production. The lipid content is at least 67% with respect to the dry matter. The alga is preferably a strain or a species of the genus *Chlorella*, the genus *Schizochytrium* or the genus *Crypthecodinium*. Whatever the culture medium, it contains yeast extracts, preferably *Saccharomyces cerevisiae*, which is preferably enriched with selenium. In this case, the culture medium comprises a selenium-containing compound. The selenium content of the culture medium is very high, namely 10 to 100% for 7.5 g/L of yeast in the culture medium, i.e. 75 to 750 mg/L of selenium.

Thus, there remains the need to increase the production of PUFA, in particular of the ω3 class, using microalgae, while simplifying extraction from the biomass. The invention aims to overcome the drawbacks of the state of the art by proposing a method for increasing the production of lipids rich in polyunsaturated fatty acids (PUFA), in particular of the ω3 class, very particularly of DHA, by using a selenium-containing compound in the culture medium.

By "rich in PUFA" is meant according to the invention comprising from 55% to 80%, preferably 60 to 75%, by weight (PUFA with respect to the total lipids). In fact, surprisingly, the applicant has noted that adding a selenium-containing compound to the culture medium of the protists can improve the production of lipids rich in polyunsaturated fatty acids, in particular of the ω3 class, very particularly of DHA, while reducing the quantity of saturated fatty acids present in these lipids of the biomass.

Thus, a subject of the invention is to optimize the production of lipids rich in PUFA, in particular of the ω3 class, more particularly of DHA, by protists, preferably microalgae, even more preferably heterotrophic marine microalgae, obtaining an alternative solution to the solutions proposed by the state of the art, but less costly and simpler to implement than the latter.

Thus, a subject of the invention is, in a first aspect, a method for enriching protists with lipids rich in polyunsaturated fatty acids, in particular and preferentially of the omega 3 (ω3) class, said method comprising the culture of protists in a culture medium comprising at least one selenium-containing compound,
the concentration in the culture medium of said selenium-containing compound being such that selenium is present at a concentration comprised between 1 and 8 mg/L.

The selenium-containing compound is preferably selected from the group formed by 2-hydroxy-4-methylselenobutyric acid or one of its salts, selenite, selenic acid, selenate, selenocysteine, selenomethionine, selenocystathionine, selenohomocysteine and seleno-adenosylselenomathionine.

The selenium-containing compound is even more preferably selected from the group formed by 2-hydroxy-4-methylselenobutyric acid (or 2-hydroxy-4-methylselenobutanoic acid) or one of its salts, selenite, selenic acid and selenomethionine.

2-hydroxy-4-methylselenobutyric acid is generally in the L, D, or D, L form.

The salt of 2-hydroxy-4-methylselenobutyric acid is preferably a calcium, zinc or magnesium salt.

In a particularly advantageous manner according to the invention, the lipids rich in polyunsaturated fatty acids are particularly rich in docosahexanoic acid (DHA).

By "rich in DHA" is meant according to the invention comprising from 45% to 70%, preferably 48 to 60%, by weight (DHA with respect to the total lipids). Unless otherwise indicated, all percentages are given here as % by weight. According to the invention, the protists are preferably microalgae of the kingdom Chromalveolata.

One of the advantages of the invention is that the enrichment with PUFA is accompanied by a depletion (also called a reduction) in saturated fatty acids produced by the protist with identical or greater total lipid content with respect to the case in which, all things being otherwise equal, the culture medium does not comprise selenium-containing compounds. This means that, in comparison with the saturated fatty acids contents obtained with the protists enriched with PUFA according to the prior art, the protist generally comprises a reduced saturated fatty acids content, i.e. generally comprised in a range from 40 to 68% with respect to the total lipids.

Without wishing to be bound by any one theory, the applicant thinks that the reduction in the saturated fatty acids content takes place to the benefit of the production of unsaturated fatty acids.

According to a first embodiment of the production method according to the invention, these microalgae are of the division Stramenopiles, preferably of the family Thraustochytrids or Labyrinthulids, even more preferably of the genus *Schizochytrium, Ulkenia, Aurantiochytrium* or *Thraustochytrium*. Preferably in this case, these microalgae are of the division Stramenopiles, preferably of the family Thraustochytrids, even more preferably of the genus *Schizochytrium, Ulkenia*, or *Thraustochytrium*.

According to a second embodiment of the production method according to the invention, these microalgae are of the division *alveolata*, preferably of the family Dinoflagellata, even more preferably of the genus *Crypthecodinium*.

According to a very particularly preferred embodiment, the microalgae are heterotrophic marine microalgae of the species *Schizochytrium limacinum* or *Schizochytrium mangrovei*, or microalgae of the species *Crypthecodinium cohnii*, preferably heterotrophic marine microalgae of the species *Schizochytrium limacinum*, or microalgae of the species *Crypthecodinium cohnii*. But heterotrophic microalgae of the species *Crypthecodinium setense, Schizochytrium aggregatum, Ulkenia profunda, Ulkenia radiata, Ulkenia visurgensis, Aurantiochytrium mangrovei, Aurantiochytrium limacinum, Thraustochytrium globosum, Thraustochytrium aureum, Thraustochytrium pachyderma, Thraustochytrium aggregatum* and/or *Thraustochytrium striatum*, preferably of the species *Crypthecodinium setense, Schizochytrium aggregatum, Ulkenia profunda, Ulkenia radiata, Ulkenia visurgensis, Thraustochytrium aureum, Thraustochytrium*

*pachyderma, Thraustochytrium aggregatum* and/or *Thraustochytrium striatum*, can also be used within the context of the invention.

By "A and/or B" is meant according to the invention A, or B, or A and B. Apart from the presence of the selenium-containing compound(s) according to the invention, the culture medium is as known to a person skilled in the art, in particular for the species concerned, i.e. it contains a nutrition medium in the chemical elements necessary for the growth of the protist (nitrogen; mineral salts; carbon; etc.)

In the particular case of 2-hydroxy-4-methylselenobutyric acid, reference may be made for the conditions of use of this acid to U.S. Pat. No. 9,017,985 by the applicant, which relates to the use of this acid for enriching a photosynthetic microorganism with selenium.

The enrichment method according to the invention is such that the concentration in the culture medium of said selenium-containing compound is such that selenium is present at a concentration comprised between 1 and 8 mg/L, for example 5 mg/L. When several selenium-containing compounds are present, this applies to the total selenium content of the medium, taking each of them into consideration.

The enrichment method is generally carried out over a duration of 96 h to 200 h, for example over a duration equal to 187 h.

The invention also relates to protists enriched with lipids rich in polyunsaturated fatty acids, in particular of the omega 3 ($\omega$3) class, obtained according to the enrichment method of the invention.

In a particularly advantageous manner according to the invention, these protists are also enriched with selenium, i.e. they comprise between 5 and 800 ppm (by weight) of selenium with respect to their total mass.

The protists enriched with lipids rich in PUFA, in particular of the $\omega$3 class, obtained by the enrichment method according to the invention are also useful as a cosmetic or nutritional agent. This selenium-containing mass enriched with lipids rich in PUFA, in particular of the $\omega$3 class, can advantageously be upgraded, very particularly for human or animal nutrition, preferentially animal. Thus, the invention also relates to the use of these protists enriched with lipids rich in PUFA, in particular of the $\omega$3 class, obtained by the enrichment method according to the invention, in nutrition or cosmetics. As a corollary, the invention relates to any food or cosmetic product comprising protists enriched with lipids rich in PUFA, in particular of the $\omega$3 class, obtained by the enrichment method according to the invention.

Thus, the protists enriched with lipids rich in PUFA, in particular of the $\omega$3 class, obtained by the enrichment method according to the invention can quite particularly be used in human or animal nutrition.

However, such a use can also be carried out after extraction treatment of the lipids rich in PUFA from the biomass or even extraction of the lipids rich in PUFA from the biomass and purification of the lipids thus extracted.

This other use is even more useful since another of the advantages of the invention is that, surprisingly, said lipids are also enriched with selenium, i.e. they comprise more than 1 ppm, even more preferably more than 2 ppm (by weight) of selenium with respect to their total mass. In all cases, they generally comprise less than 30 ppm of selenium relative to their total mass. The presence at this relatively high quantity of selenium in the lipids is another characteristic of the method according to the invention. It is thus possible to use the term "selenium-containing microalgal lipids" or "selenium-containing lipids". Extraction can be carried out by any extraction method known to a person skilled in the art, such as extraction by at least one organic solvent or extraction by carbon dioxide in a supercritical state.

Thus, a subject of the invention, according to a second aspect, is a method for producing lipids rich in polyunsaturated fatty acids, in particular of the omega 3 ($\omega$3) class, successively comprising:

a method for enriching protists with lipids rich in polyunsaturated fatty acids, in particular of the $\omega$3 class, according to the invention, so as to obtain protists enriched with lipids rich in polyunsaturated fatty acids, in particular of $\omega$3 class; and a method for treating protists enriched with lipids rich in polyunsaturated fatty acids, in particular of the $\omega$3 class, by extracting from the biomass lipids rich in polyunsaturated fatty acids, in particular of the $\omega$3 class, so as to obtain (selenium-containing) lipids rich in polyunsaturated fatty acids, in particular of the $\omega$3 class, and a selenium-containing biomass depleted of lipids.

The selenium-containing biomass depleted of lipids rich in PUFA obtained after this extraction, can also be advantageously used, among other things in generally human or animal nutrition, preferably animal.

The method for treating protists enriched with lipids rich in polyunsaturated fatty acids, in particular of the $\omega$3 class, thus consists of extracting from the biomass lipids rich in polyunsaturated fatty acids, most often and preferably followed by purification of the lipids thus extracted (separated from the biomass) rich in polyunsaturated fatty acids, in particular of the $\omega$3 class. This treatment method is generally followed by analysis of the profile of the lipids thus obtained.

The method for extracting the lipids from the biomass is known to a person skilled in the art and is, for example, specified in the example below.

Thus, a subject of the invention, according to a third aspect, is lipids rich in polyunsaturated fatty acids, in particular of the omega 3 ($\omega$3) class, obtained according to the production method of the invention, which are, advantageously, also enriched with selenium and for this reason qualified as "selenium-containing lipids".

The lipids can be used as they are, most often in human or animal nutrition.

Thus, the method for producing lipids rich in polyunsaturated fatty acids, in particular of the $\omega$3 class, according to the invention, comprises implementing the enrichment method according to the invention, this enrichment method having the same characteristics as those explained above.

Finally, the invention relates to any food or cosmetic product comprising lipids rich in polyunsaturated fatty acids, in particular of the omega 3 ($\omega$3) class, obtained by the production method according to the invention.

The invention will be better understood in the light of the embodiment examples below, with reference to the attached drawings in which.

Figure 3:
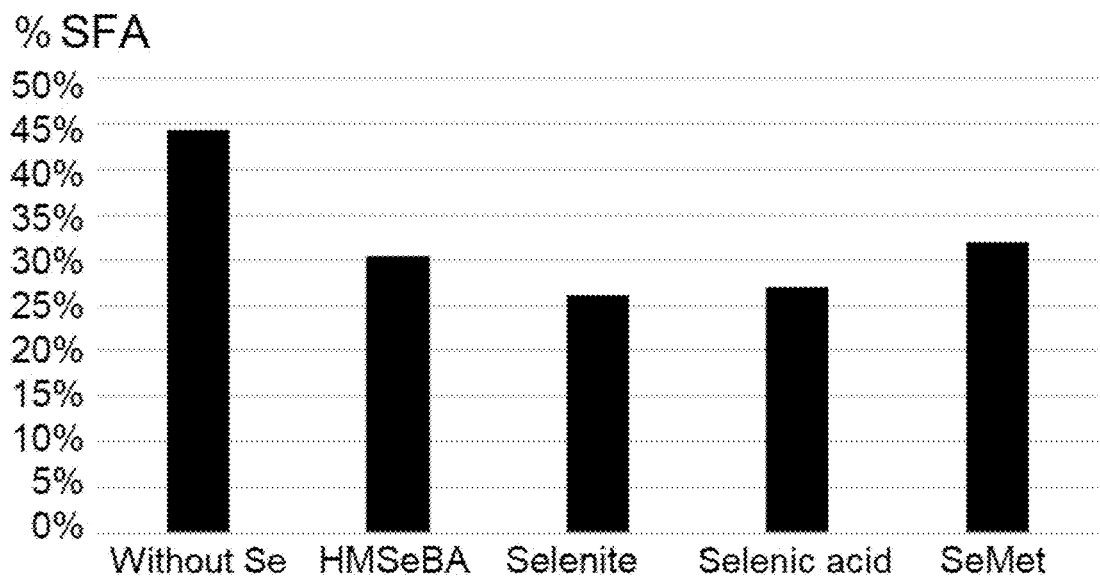
Figure 4:
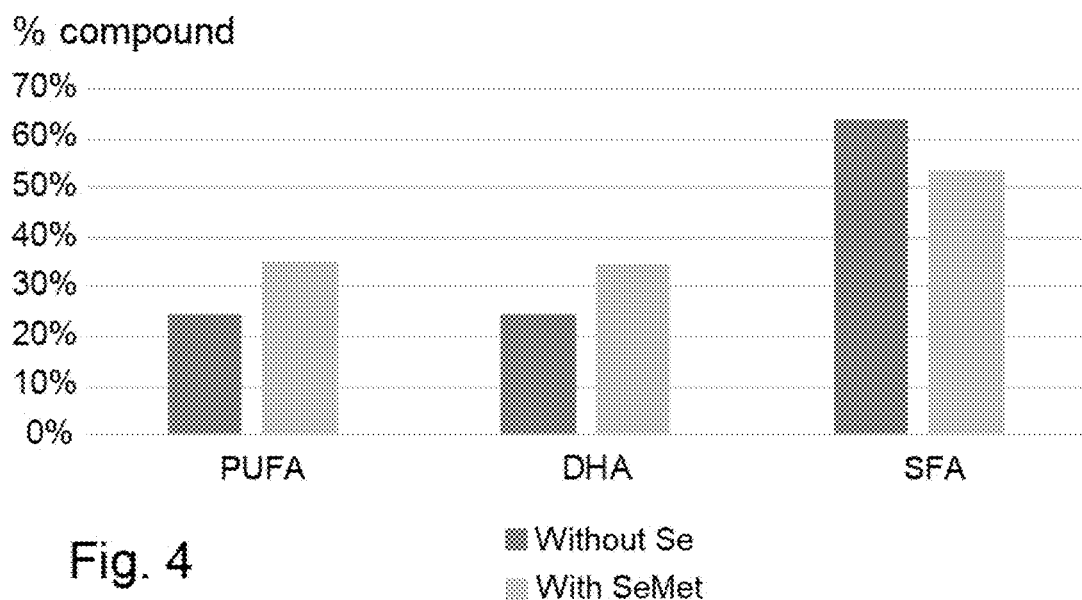

FIG. 3 is a graph giving the weight percent of saturated fatty acids (SFA) in the total lipids for *Schizochytrium limacinum* after incubation for 187 h; and FIG. 4 is a graph giving the weight percent of polyunsaturated fatty acids (PUFA) in the total lipids, the weight percent of docosahexanoic acid (DHA) in the total lipids and the weight percent of saturated fatty acids (SFA) in the total lipids, for *Crypthecodinium cohnii* after incubation for 187 h.

FIGS. 1 to 4 are explained in Examples 1 and 2 below.

EXAMPLES

The following examples illustrate the invention without, however, limiting its scope.

Example 1: Culture of *Schizochytrium* Protist in a Medium Containing Separately 2-Hydroxy-4-Methylselenobutyric Acid (HMSeBA); Selenite; Selenic Acid; or Selenomethionine This culture has led to improvement in the production of polyunsaturated fatty acids and of DHA in particular.

*Schizochytrium* is a protist, and more precisely a heterotrophic Thraustochytride microalga.

A strain of *Schizochytrium limacinum* ATCC-MYA1381 was obtained from the ATCC bank (www.atcc.org).

The growth characteristics as well as the production of lipids by *Schizochytrium limacinum* were measured in the presence of different forms of selenium and compared in the absence of such additives (control referenced "Without Se" in the figures).

Pre-culture of the strain *Schizochytrium limacinum* ATCC-MYA1381 was carried out in standard liquid medium, the composition of which is given in Table 1. To this end, starter cultures of 50 mL were started in a 250 mL Erlen flask from a colony isolated on 633 M3 chytrid agar (www.atcc.org) and cultured at 25° C.±1° C. in heterotrophy for 48 h in this standard liquid medium. The 100 mL inoculum is then started in a 500 mL Erlen flask from these "starter" cultures at an initial concentration of $1.0 \times 10^6$ cells/m/L in the same culture conditions as the latter for 4 days. The cultures were continuously aerated by orbital stirring at 100 rpm ("revolutions per minute").

The cultures for enrichment with selenium-containing compounds were started from the inoculum at an initial concentration of $1.0 \times 10^6$ cells/mL for a final volume of 400 mL in a 2.0 L Erlen flask at 25° C.±1° C. in heterotrophy for 187 h. The cultures were continuously aerated by orbital stirring at 100 rpm. Enrichment was carried out at TO by the addition of concentrated selenium solution (2-hydroxy-4-methylselenobutyric acid solution sold by the company Tetrahedron at 0.0125 g/L referenced «HMSeBA» in FIGS. 1 to 3, sodium selenite 0.0110 g/L referenced "Selenite" in FIGS. 1 to 3, selenic acid 0.0082 g/L referenced "Selenic acid" in FIGS. 1 to 3 and selenomethionine 0.0124 g/L referenced "SeMet" in FIGS. 1 to 3) for a final concentration of 5 mg of selenium/L in the medium, whatever the source of the selenium-containing compound.

The *Schizochytrium limacinum* biomass was then harvested after incubation for 72 h and 187 h.

TABLE 1

Summary of the concentrations of each reagent composing the standard liquid culture medium

| Reagents | Final concentration (g/L) |
|---|---|
| Artificial seawater | 33 |
| Yeast extract | 8.7 |
| Glucose monohydrate (G8270 Sigma) | 17.0 |

Artificial seawater is a common commercial product; in this case it was the product "Instant Ocean Salt" from the company AQUARIUM SYSTEMS. Its composition is given below by way of information: $Na^+$ (0.35 g/L); $K^+$ (0.01 g/L); $Mg^{2+}$ (0.04 g/L); $Ca^{2+}$ (0.01 g/L); $Sr^+$ (0.00054 g/L); Cl (0.641 g/L); S ($SO4^{2-}$) (0.07 g/L); P ($PO_4$) (0.000157 mg/L); N (NO3) (0.002 mg/L); N (NH4) (0.006 mg/L); Si ($SiO_3$) (0.0105 mg/L); Li (0.0124 mg/L); Si (0.0148 mg/L); Mo (0.0057 mg/L); Ba (0.00385 mg/L); V (0.0048 mg/L); Ni (0.00329 mg/L); Cr (0.0129 mg/L); Al (0.214 mg/L); Cu (0.00377 mg/L); Zn (0.00108 mg/L); Mn (0.00218 mg/L); Fe (0.000442 mg/L); Cd (0.000890 mg/L); Pb (0.0144 mg/L); Co (0.00253 mg/L); Ag (0.00819 mg/L); Ti (0.00106 mg/L). Yeast extract is a standard commercial product provided by the company Merck.

Culture Monitoring

The total concentration of biomass was monitored by measuring the dry mass (filtration on GFC filter, Whatman, then drying in an oven under vacuum, 70° C. and −0.8 bar (80 kPa), for 24 h minimum before weighing). $10^7$ cells/mL were extracted in order to quantify the total lipids. The method for extracting lipids is known to a person skilled in the art and is as described by the publication "Bligh E. G. & Dyer W. J., *A rapid method of total lipid extraction and purification, Can. J. Biochem. Physiol* 37 1959 911-917", this method having been slightly adapted for microalga cells. Thus, for each measurement, approximately 10 mL of culture (biomass and medium), freshly sampled, was washed with demineralized water so as to remove the extracellular salts before lyophilization, then placed in a glass tube and centrifuged for 10 mins at 3600 g and at 4° C. After centrifugation, the supernatant was removed and the pellet containing the cells was lyophilized. Extraction was carried out with 6 mL of a monophasic $CHCl_3$/MeOH (chloroform/methanol) mixture in proportions of 2/1 (V/V). In order to ensure complete extraction of the lipids, the tube was kept under stirring on a rocker for 6 hours in darkness, then stored at −20° C. before being analyzed by GC-FID (gas chromatography with flame ionization detection) in order to determine the quantity and the profiles of the total fatty acids extracted.

Figure 1:
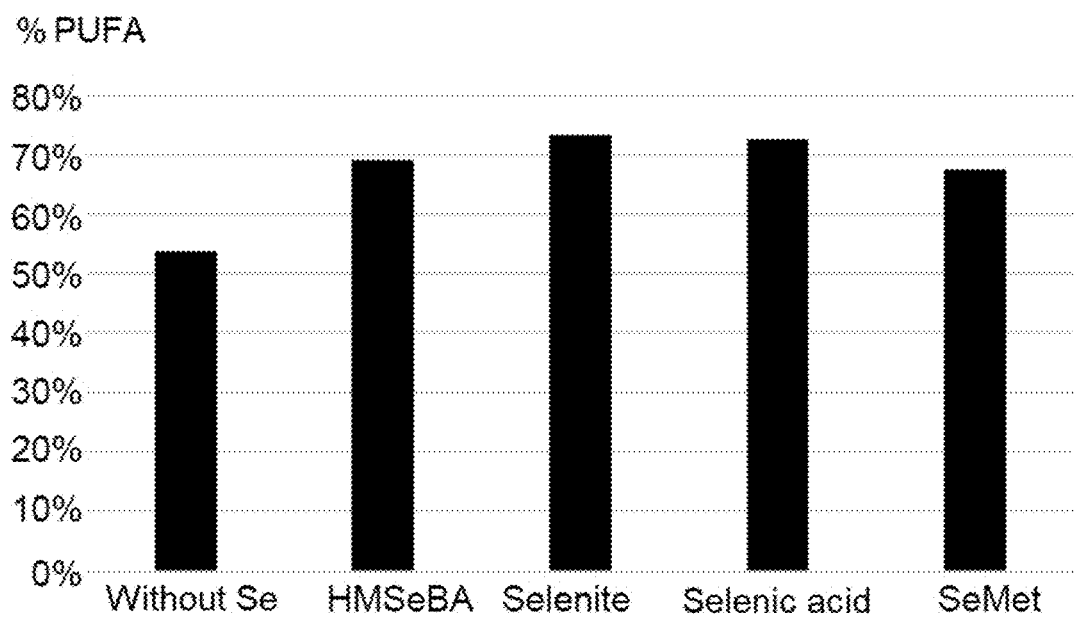
FIG. 1 is a graph giving the weight percent of polyunsaturated fatty acids (PUFA) in the total lipids for *Schizochytrium limacinum* after incubation for 187 h.
Figure 2:
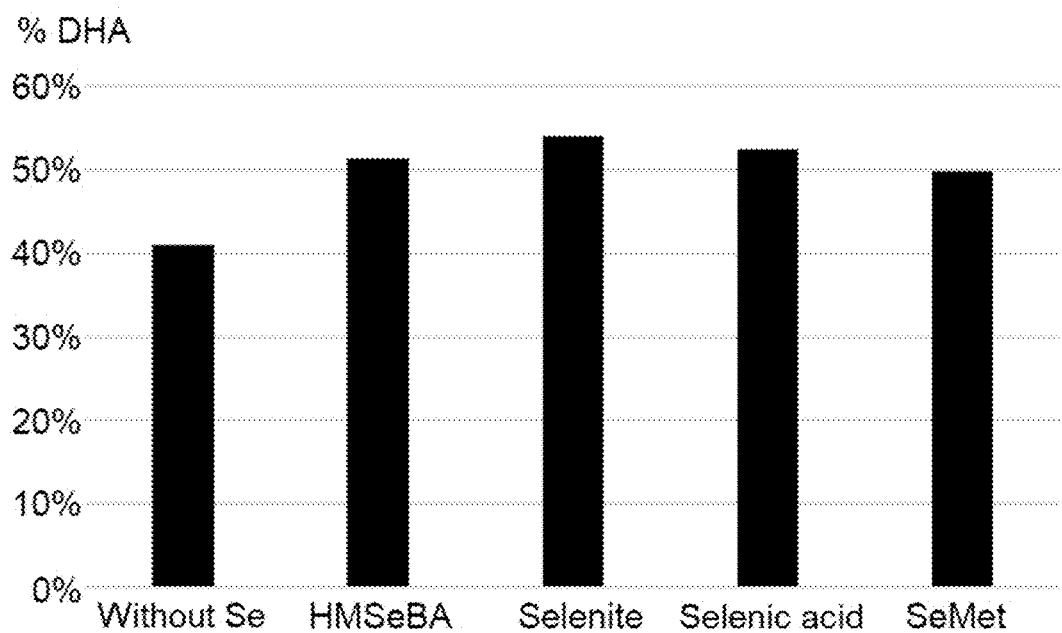
FIG. 2 is a graph giving the weight percent of docosahexaenoic acid (DHA) in the total lipids for *Schizochytrium limacinum* after incubation for 187 h.

The results obtained are shown in FIGS. 1, 2 and 3 which give respectively, for *Schizochytrium limacinum* after incubation for 187 h, the percentage of PUFA of total lipids, the percentage of DHA in the total lipids and the percentage of SFA in the total lipids on the y-axis, for each of the selenium-containing sources shown on the x-axis.

It has been noted that the presence of a selenium-containing compound at 5 mg/L in the culture medium made it possible to obtain a percentage of PUFA markedly higher than that of the control (at least 67% against 53%), whatever the selenium-containing species used, the most interesting result being given by selenite (73%).

It has also been noted that the presence of a selenium-containing compound at 5 mg/L in the culture medium made it possible to obtain a percentage of DHA markedly higher than that of the control (at least 50% against 41%), whatever the selenium-containing species used, the most interesting result being given by selenite (54%).

Finally, it has been noted that the presence of a selenium-containing compound at 5 mg/L in the culture medium made it possible to obtain a percentage of SFA markedly lower than that of the control (at least 31% against 44%), whatever the selenium-containing species used, the most interesting result being given by selenite (26%).

Example 2. Culture of *Crypthecodinium cohnii* Protist in a Medium Containing Selenomethionine This culture has led to improvement in the production of polyunsaturated fatty acids and of DHA in particular.

It was produced in the same way as in Example 1, except that the protist is *Crypthecodinium cohnii* instead of *Schizochytrium limacinum*, and that a single source of selenium was used: selenomethionine ("SeMet").

*Crypthecodinium cohnii* is a protist, and more precisely a heterotrophic microalga. The strain *Crypthecodinium cohnii* CCMP 316 was obtained from the NCMA bank (https://ncma.bigelow.org).

The results obtained are shown in FIG. 4 which gives respectively, for *Crypthecodinium cohnii* after incubation for 187 h, the percentage of compound in the total lipids on the y-axis, for each of the compounds (PUFA, DHA and SFA) shown on the x-axis, in the presence of selenomethionine (reference "With SeMet"), or in the absence of a selenium-containing compound (reference "Without Se").

It has been noted that the presence of selenomethionine at 5 mg/L of selenium in the culture medium has made it possible to obtain a percentage of PUFA markedly higher than that of the control (35% against 25%).

It has also been noted that the presence of selenomethionine at 5 mg/L of selenium in the culture medium has made it possible to obtain a percentage of DHA markedly higher than that of the control (34% against 24%).

Finally, it has been noted that the presence of selenomethionine at 5 mg/L of selenium in the culture medium has made it possible to obtain a percentage of SFA markedly lower than that of the control (53.5% against 64%).

Moreover, an increase in the total lipid content in the dry biomass has been noted, due to the use of selenomethionine. In fact, a quantity of 34% more total lipids is obtained using the selenium-containing culture medium relative to the control medium.

The invention claimed is:

1. Protists comprising from 55% to 80% by weight of polyunsaturated fatty acids with respect to total lipids, said protists being obtained by a method which comprises culturing protists in a culture medium comprising at least one selenium-containing compound, wherein the concentration of said selenium-containing compound in the culture medium being such that the concentration of selenium in the culture medium is comprised between 1 and 8 mg/L.

2. Protists of claim 1, wherein said polyunsaturated fatty acids are of the omega 3 class.

3. Protists of claim 1, wherein the selenium-containing compound is selected from the group formed by 2-hydroxy-4-methylselenobutyric acid or one of its salts, selenite, selenic acid, selenate, selenocysteine, selenomethionine, selenocystathionine, selenohomocysteine and selenoadenosylselenomathionine.

4. Protists of claim 3, wherein the selenium-containing compound is selected from 2-hydroxy-4-methylselenobutyric acid or one of its salts, selenite, selenic acid and selenomethionine.

5. Protists of claim 1, wherein the protists are of the division Stramenopiles.

6. Protists of claim 1, wherein the protists are of the division *alveolata*.

7. Protists of claim 1, wherein the protists are heterotrophic marine microalgae of the species *Schizochytrium limacinum* or *Schizochytrium mangrovei*, or microalgae of the species *Crypthecodinium cohnii*.

8. Protists of claim 7, wherein the heterotrophic microalgae are microalgae of the species *Schizochytrium limacinum* or microalgae of the species *Crypthecodinium cohnii*.

9. Food or cosmetic product comprising protists according to claim 1.

10. Food or cosmetic product comprising protists according to claim 2.

11. Lipids comprising from 55% to 80% by weight of polyunsaturated fatty acids, with respect to the total lipids, said lipids being obtained by a method comprising:
   treating protists of claim 1 by extracting from the biomass lipids comprising from 55% to 80% by weight of polyunsaturated fatty acids, with respect to the total lipids so as to obtain lipids comprising from 55% to 80% by weight of polyunsaturated fatty acids, with respect to the total lipids and a selenium-containing biomass depleted of lipids.

12. Lipids of claim 11, wherein extraction is followed by purification of the lipids thus extracted comprising from 55% to 80% by weight of polyunsaturated fatty acids, with respect to the total lipids.

13. Protists according to claim 1, wherein said lipids comprise more than 1 ppm of selenium with respect to their total mass.

14. Protists according to claim 1, wherein said lipids comprise more than 2 ppm of selenium with respect to their total mass.

15. Lipids comprising from 55% to 80% by weight of polyunsaturated fatty acids, with respect to the total lipids and more than 1 ppm by weight, of selenium with respect to their total mass.

16. Lipids of claim 15, being obtained by a method comprising:
   treating protists with lipids comprising from 55% to 80% by weight of polyunsaturated fatty acids with respect to the total lipids by extracting from the biomass lipids so as to obtain lipids comprising from 55% to 80% by weight of polyunsaturated fatty acids, with respect to the total lipids and a selenium—containing biomass depleted of lipids.

17. Lipids of claim 16, wherein extraction is followed by purification of the lipids thus extracted comprising from 55% to 80% by weight of polyunsaturated fatty acids, with respect to the total lipids.

18. Food or cosmetic product comprising selenium—containing lipids according to claim 15.

19. Food product according to claim 18, for human or animal nutrition.

* * * * *